US010023535B2

(12) United States Patent
Bertolini et al.

(10) Patent No.: US 10,023,535 B2
(45) Date of Patent: Jul. 17, 2018

(54) METHOD FOR THE PREPARATION OF 1-(2-HALOGEN-ETHYL)-4 PIPERIDINE-CARBOXYLIC ACID ETHYL ESTERS

(71) Applicant: LABORATORIO CHIMICO INTERNAZIONALE S.P.A., Milan (IT)

(72) Inventors: Giorgio Bertolini, Rodano (IT); Corrado Colli, Rodano (IT); Aldo Bianchi, Solaro (IT); Federica Colombo, Milan (IT); Stefano Maiorana, Milan (IT); Filippo Nisic, Milan (IT)

(73) Assignee: OLON S.P.A., Rodano (MI) (IT)

( * ) Notice: Subject to any disclaimer, the term of this patent is extended or adjusted under 35 U.S.C. 154(b) by 0 days.

(21) Appl. No.: 15/520,256

(22) PCT Filed: Oct. 22, 2015

(86) PCT No.: PCT/IB2015/058145
§ 371 (c)(1),
(2) Date: Apr. 19, 2017

(87) PCT Pub. No.: WO2016/071792
PCT Pub. Date: May 12, 2016

(65) Prior Publication Data
US 2017/0313657 A1    Nov. 2, 2017

(30) Foreign Application Priority Data
Nov. 3, 2014  (IT) .............................. MI2014A1875

(51) Int. Cl.
*C07D 211/62* (2006.01)
*C07C 22/00* (2006.01)
(Continued)

(52) U.S. Cl.
CPC ............ *C07D 211/62* (2013.01); *C07C 22/00* (2013.01); *C07C 209/24* (2013.01); *C07D 211/06* (2013.01); *C07F 13/00* (2013.01)

(58) Field of Classification Search
USPC ........................................................ 546/242
See application file for complete search history.

(56) References Cited

U.S. PATENT DOCUMENTS

| 5,696,267 A | * | 12/1997 | Reichard | .............. | C07D 211/52 546/217 |
| 2004/0157851 A1 | * | 8/2004 | Haddach | .............. | C07D 471/16 514/250 |

(Continued)

FOREIGN PATENT DOCUMENTS

| WO | 2005087764 A1 | 9/2005 |
| WO | 2005104745 A2 | 11/2005 |
| WO | 2014027045 A1 | 2/2014 |

OTHER PUBLICATIONS

Chemical Abstracts CASREACT Record for reaction of example 302 of WO 2008133155. 1 page. (Year: 2008).*

(Continued)

*Primary Examiner* — Daniel R Carcanague
(74) *Attorney, Agent, or Firm* — Lucas & Mercanti, LLP

(57) ABSTRACT

The present invention refers to a process for the preparation of 1-(2-halogen-ethyl)-4-piperidinecarboxylic acid ethyl esters, in particular of 1-(2-chloroethyl)-4 piperidinecarboxylic acid ethyl ester, a versatile synthesis intermediate, particularly useful as an intermediate compound in the synthesis of umeclidinium.

16 Claims, 1 Drawing Sheet

(51) Int. Cl.
    *C07F 13/00*     (2006.01)
    *C07D 211/06*     (2006.01)
    *C07C 209/24*     (2006.01)

(56) References Cited

U.S. PATENT DOCUMENTS

| | | | | |
|---|---|---|---|---|
| 2006/0223792 | A1 | 10/2006 | Butler et al. | |
| 2010/0105679 | A1* | 4/2010 | Guzzo | C07D 401/04 514/234.5 |
| 2010/0113391 | A1* | 5/2010 | Koga | C07D 217/24 514/63 |

OTHER PUBLICATIONS

Moormann; Synthetic Communications 1993, 23, 789-795.*
Abdel-Magid et al., "Reductive Amination of Aldehydes and Ketones with Sodium Triacetoxyborohydride. Studies on Direct and Indirect Reductive Amination Procedures", J.Org. Chem., 1996, vol. 61, No. 11, pp. 3849-3862.
International Search Report and Written Opinion for International Application No. PCT/IB2015/058145 (dated Feb. 4, 2016) (15 Pages).
Italian Search Report for Italian Application No. MI20141875 (dated Feb. 2, 2015) (3 Pages).

* cited by examiner

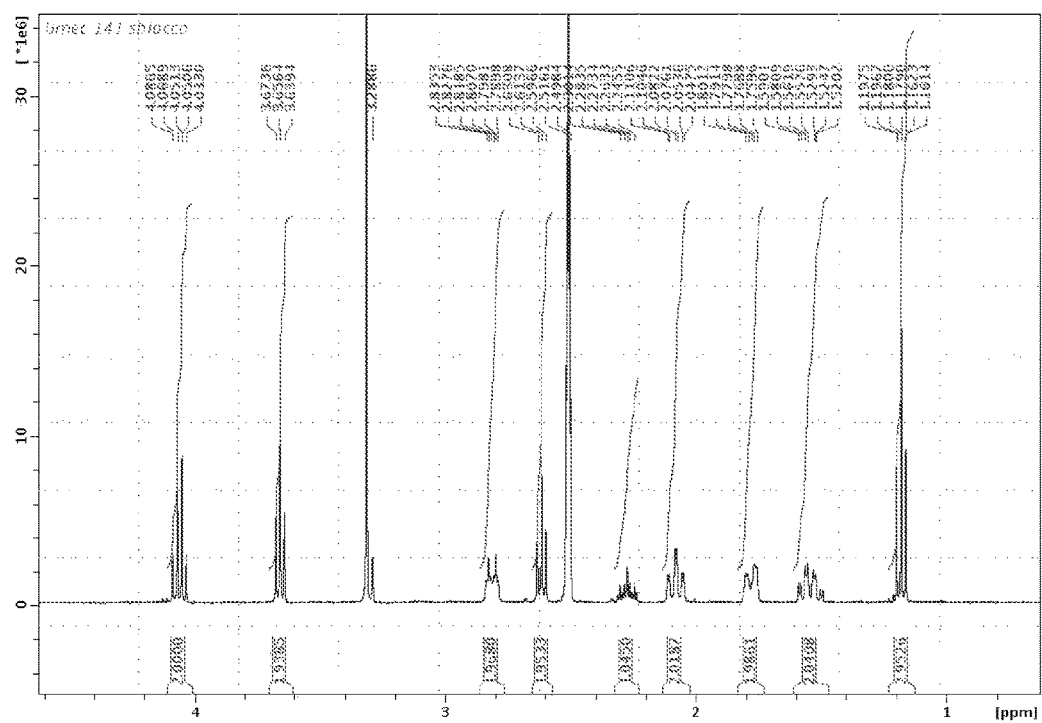

METHOD FOR THE PREPARATION OF 1-(2-HALOGEN-ETHYL)-4 PIPERIDINE-CARBOXYLIC ACID ETHYL ESTERS

CROSS-REFERENCE TO RELATED APPLICATIONS

This application is a 371 of PCT/IB2015/058145, filed Oct. 22, 2015, which claims the benefit of Italian Patent Application No. MI2014A001875, filed Nov. 3, 2014.

TECHNICAL FIELD

Umeclidinium, in particular umeclidinium bromide, is a compound used in the therapy of individuals suffering from chronic obstructive pulmonary disease. A key intermediate in its synthesis is 1-(2-chloroethyl)-4 piperidinecarboxylic acid ethyl ester, of formula (I)

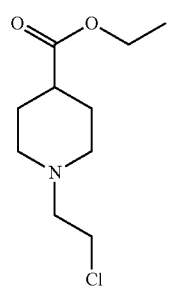
(I)

of which some synthesis are described in the literature.

In particular, WO2005/104745 describes a process for the preparation of compound of formula (I) comprising reacting 1-bromo-2-chloroethane and ethyl-isonipecotate as follows:

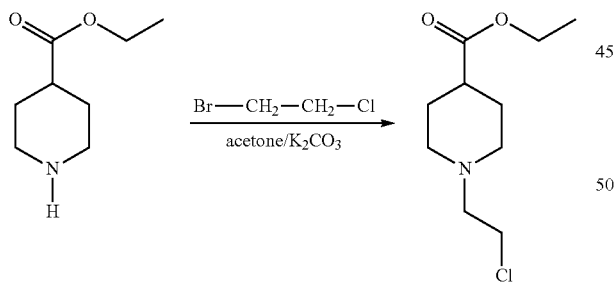

However, such a reaction provides very low yields (about 38%), due to the simultaneous dimerization reaction leading to the 1,1'-(ethane-1,2-diyl)bis(piperidine-4-carboxylate) compound. In addition, the compound obtained by this process is significantly impure and must be necessarily purified by chromatography, a purification process which is not particularly suitable for an industrial synthesis.

In order to overcome the dimerization problem and the resulting low yields, WO2014/027045 describes a two-steps process for the preparation of compound of formula (I), in particular by the following reactions:

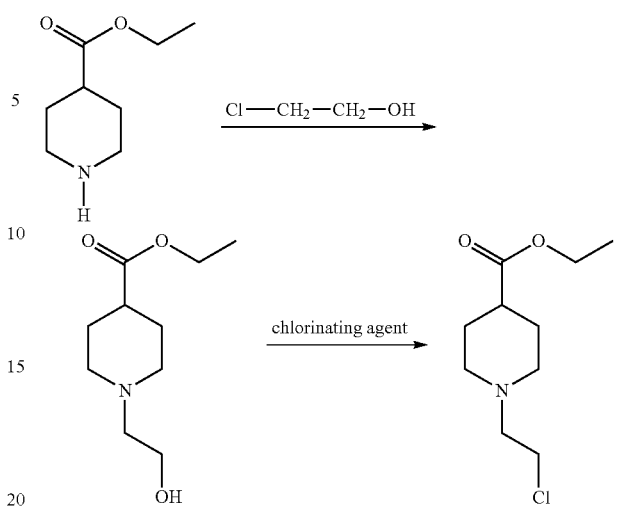

It is clear that such a synthesis, although leading to better yields with respect to those described in WO2005/104745, requires two reaction steps and the separation of the hydroxylated intermediate by distillation of the reaction solvents, prior to the reaction with the chlorinating agent.

BRIEF DESCRIPTION OF THE DRAWINGS

FIG. 1 displays the $^1$H-NMR spectrum of the compound of example 1.

OBJECTS OF THE INVENTION

It is an object of the invention to provide a process for the preparation of a derivative of 1-(2-ethyl)-4 piperidinecarboxylic acid ethyl ester, in particular of 1-(2-chloroethyl)-4 piperidinecarboxylic acid ethyl ester, which is fast, provides good yields and excellent purity and is industrially convenient.

Description of the Invention

According to one of its aspects, the invention is directed to a process for the preparation of a compound of formula (I)

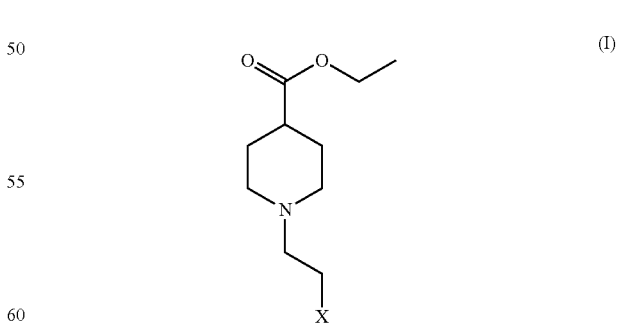
(I)

wherein X is a leaving group, comprising carrying out a reductive amination of ethyl-isonipecotate with a X-acetaldehyde, wherein X is as defined above, in a solvent system, in the presence, or with subsequent addition, of a reducing agent, according to scheme (I) below:

Scheme (I)

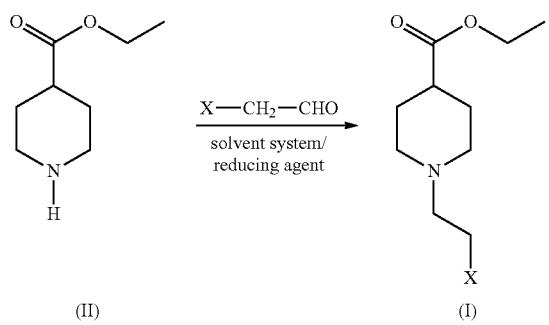

(II)    (I)

The definition of "leaving group" is well known to skilled in the art and "X-acetaldehyde" means herein a compound of formula X—CH$_2$—CHO wherein X is a leaving group, e.g. bromine or chlorine, preferably X-acetaldehyde is chloroacetaldehyde.

According to a preferred embodiment, the solvent system comprises at least one solvent suitable for the reductive amination reaction, e.g. a solvent selected from lower alcohols, such as C$_1$-C$_4$ alcohols, as methanol, ethanol, isopropanol, tert-butanol, and the like; and acetonitrile and aliphatic or cyclic ethers, such as THF.

Alternatively, it would be in any case possible to use other solvents, such as chlorinated solvents, as dichloromethane, 1,2-dichloroethane and the like. However such solvents, which are described in the literature for this kind of reactions, are toxic, whereas the process of the invention has the advantage of proceeding very well also in low-toxicity solvents such as those mentioned above.

According to a preferred embodiment, the reductive amination reaction of the invention is carried out under acidic catalysis, and in this case the solvent system also comprises an acid, advantageously a weak acid, such as, e.g., a carboxylic acid. Suitable acids include acetic acid and formic acid, with acetic acid being preferred. According to a most preferred embodiment, the solvent system is a mixture comprising a solvent and acetic acid, advantageously in a solvent/acetic acid ratio of at least 8-10/1 (v/v) or higher, for example 12-15/1 or even higher.

Preferred solvent systems are methanol/acetic acid/acetonitrile and acetic acid systems, preferably in the ratios reported above.

According to another embodiment, the solvent system is only made of one weak acid as defined above such as, e.g., acetic acid.

Preferably, the ethyl-isonipecotate/X-acetaldehyde molar ratio is at least equimolar, preferably X-acetaldehyde is used in excess, e.g. the ratio is about 1/1-2, e.g. 1/1 or 1/1.5.

According to a preferred embodiment, the X-acetaldehyde is chloroacetaldehyde and it is used in an aqueous solution, e.g. in a 50% (w/w) solution. The possibility of using an aqueous solution of X-acetaldehyde is surprising, since the reductive amination reactions are usually carried out in stringently anhydrous conditions. In this case, however, it has been observed that the process of the invention results in good yields also in the presence of water, provided that the reducing agent is added to the reaction mixture from the beginning. The compound is directly obtained in an extremely pure form and such a result is unexpected and surprising. It is known that the use of chloroacetaldehyde for the reductive amination reaction is not expected for the skilled in the art, since such a reagent can chemically behave either as an aldehyde and as a chloride. If it would behave as a chloride it would be an alkylating agent, in particular for the amines. Moreover, since the reaction is carried out in the presence of water (which usually inhibits the formation of the Schiff base), it is expected that the alkylating function would be dominant. On the other hand and unexpectedly, the reaction leads to a high-purity single product, showing that the unfavorable reactivity of the reaction environment is, on the contrary, unexpectedly favored. In other words, the result of the reaction is opposite to expectations of the skilled in the art and leads to the desired compound with significant yield and purity. As an alternative to X-acetaldehyde it is also possible to use hydrated forms, acetals or hemiacetals thereof.

The expression "reducing agent" means herein a reducing agent suitable for the reduction of imines and that does not reduce the starting aldehyde, for example a compound selected from sodium cyanoborohydride (NaCNBH$_3$); sodium triacetoxyborohydride (NaBH(OAc)$_3$); 3-pyridineborane (pyr-BH3); Ti(Oi-Pr)$_4$/NaBH$_4$: borohydride supported on resins; Zn(BH$_4$)$_2$/SiO$_2$; Bu$_3$SnH/SiO$_2$; or phenyl-SiH$_4$/Bu$_2$SnCl$_2$. Sodium cyanoborohydride (NaCNBH$_3$) and sodium triacetoxyborohydride (NaBH(OAc)$_3$) are preferred reducing agents and sodium cyanoborohydride is a particularly preferred reducing agent for the reaction reported above.

The amounts of reducing agent depend upon the agent employed and the skilled in the art is certainly able to calculate them. As an example, it is possible to use nearly equimolar amounts of sodium cyanoborohydride relative to the starting compound or even lower amounts. Molar amounts of ethyl-isonipecotate/X-acetaldehyde/sodium cyanoborohydride can be, e.g., 1/1-1.5/0.3-1.5, advantageously about 1/1-1.5/0.5-1, more preferably 1/1-1.5/1. On the other hand, for the triacetoxyborohydride it is possible to use higher amounts, e.g. the molar amounts of ethyl-isonipecotate/X-acetaldehyde/triacetoxyborohydride can be, e.g., 1/1-1.5/3-7, advantageously about 1/1-1.5/4-6.

It has been observed that by adding a halogen salt to the reaction mixture, e.g. an alkali metal or an alkali earth metal chloride, e.g. lithium chloride or similar compounds, when using the chloroacetaldehyde, it is possible to obtain the desired compound with higher yields and lower impurities. The amount of said salt is not critical, as an example it can be added in an amount of 10-50% (w/w) or even up to equimolar amounts relative to the starting isonipecotate.

When the process of the invention occurs in the presence of water, e.g., but not exclusively, when working with aqueous X-acetaldehyde, the presence of some reducing agents (such as NaCNBH$_3$ and other listed above), aids the completion of the reaction and increases the purity of the obtained product.

However, working in an environment poor of water, it is possible to form the imine and later reduce it by any reaction known in the art for this kind of reaction. Therefore, the expression "in presence, or with later addition, of a reducing agent" means that, when working in an aqueous environment, it is preferable to add the reducing agent from the beginning of the amination reaction in order to favor its completion.

The process of scheme (I) can occur at room temperature and it is completed in few hours (usually, the reaction is complete within 4 hours). It is possible to cool down the reaction mixture, e.g. in an ice bath, when adding the reducing agent in order to avoid an excessive increase of the internal temperature. The skilled in the art can control the development according to known techniques, e.g. by UPLC (ultra-performance liquid chromatography).

At the end of the reaction the solvents are evaporated and compound of formula (I) is usually obtained already at high purity and it can be directly used without the need of further processing, opposite to what is described in the prior art. However, if desired and needed, the compound can be purified according to conventional techniques, e.g. by simple filtration on silica or by precipitation as a salt, e.g. as hydrochloride. Examples of the process of the invention are provided in the "Experimental section" below with a merely illustrative and not-limiting purpose.

It will be clear that the process of the invention provides compound of formula (I) with excellent yields and high purity and by means of a simple reductive amination reaction without the need of intermediate isolation and/or purification steps, and therefore represents a significant improvement in the industrial field and a valuable alternative to the processes of the prior art.

EXPERIMENTAL SECTION

Example 1

A single-neck flask is charged with ethyl-isonipecotate (369.6 mg; 2.3 mmoles), 6.7 ml of a methanol/acetic acid mixture (10/1) are added and the 50% chloroacetaldehyde aqueous solution (180.5 mg; 2.3 mmoles) is added dropwise. The solution is cooled to 0° C. in an ice bath and NaCNBH$_3$ (144.5 mg; 2.3 mmoles) is added portionwise. It is stirred at room temperature for 2 hrs and the development of the reaction is checked by UPLC. The solvent is evaporated at 40° C. under reduced pressure, the aqueous phase is made basic with K$_2$CO$_3$, extracted with AcOEt and dried on Na$_2$SO$_4$. The solvent is evaporated at 40° C. under reduced pressure and 456.7 mg of compound of formula (I) are thus obtained wherein X is chlorine (90% yield).

$^1$H-NMR Analysis

The product obtained in example 1 has been analyzed by $^1$H-NMR in DMSO. The spectrum, reported in FIG. 1, only present signals related to the structure of the desired compound, thus showing that the compound is pure ($^1$H-NMR, 400 MHz).

Example 2

A single-neck flask is charged with ethyl-isonipecotate (443 mg; 2.8 mmoles), 8 ml of an acetonitrile/acetic acid mixture (10/1) are added and the 50% chloroacetaldehyde aqueous solution (219.8 mg; 2.8 mmoles) is added dropwise. The solution is cooled to 0° C. in an ice bath and NaBH(OAc)$_3$ (2.4 mg; 11.3 mmoles) is added portionwise. It is stirred at room temperature for 2 hrs and the development of the reaction is checked by UPLC. The solvent is evaporated at 40° C. under reduced pressure, the aqueous phase is made basic with K$_2$CO$_3$, extracted with AcOEt and dried on Na$_2$SO$_4$. The solvent is evaporated at 40° C. under reduced pressure and compound of formula (I) is thus obtained wherein X is chlorine.

Example 3

A single-neck flask is charged with ethyl-isonipecotate (468.2 mg; 3 mmoles), 8.6 ml of a methanol/acetic acid mixture (10/1) are added and the 50% chloroacetaldehyde aqueous solution (235.5 mg; 3 mmoles) is added dropwise. The solution is cooled to 0° C. in an ice bath and NaBH(OAc)$_3$ (2.5 mg; 12 mmoles) is added portionwise. It is stirred at room temperature for 2 hrs and the development of the reaction is checked by UPLC. The solvent is evaporated at 40° C. under reduced pressure, the aqueous phase is made basic with K$_2$CO$_3$, extracted with AcOEt and dried on Na$_2$SO$_4$. The solvent is evaporated at 40° C. under reduced pressure and compound of formula (I) is thus obtained wherein X is chlorine.

Example 4

A single-neck flask is charged with ethyl-isonipecotate (349.7 mg; 2.2 mmoles), 6.3 ml of methanol/acetic acid (10/1) are added and the 50% chloroacetaldehyde aqueous solution (172.7 mg; 2.2 mmoles) is added dropwise. The solution is cooled to 0° C. in an ice bath and NaCNBH$_3$ (69.1 mg; 1.1 mmoles) is added portionwise. It is stirred at room temperature for 2 hrs and the development of the reaction is checked by UPLC. The solvent is evaporated at 40° C. under reduced pressure, the aqueous phase is made basic with K$_2$CO$_3$, extracted with AcOEt and dried on Na$_2$SO$_4$. The solvent is evaporated at 40° C. under reduced pressure and compound of formula (I) is thus obtained wherein X is chlorine.

Example 5

A single-neck flask is charged with ethyl-isonipecotate (927.8 mg; 5.9 mmoles), 16.8 ml (0.35 M) of methanol/acetic acid (10/1) are added and the 50% chloroacetaldehyde aqueous solution (463.1 mg; 5.9 mmoles) is added dropwise. The solution is cooled to 0° C. in an ice bath and NaCNBH$_3$ (370.9 mg; 5.9 mmoles) is added portionwise. It is stirred at room temperature for 2 hrs and the development of the reaction is checked by UPLC. The solvent is evaporated at 40° C. under reduced pressure, the residue is taken up with 2N HCl (10 ml) and left under stirring for 30 min. It is extracted with AcOEt (2×20 ml), the aqueous phase is made basic with K$_2$CO$_3$, extracted with AcOEt and dried on Na$_2$SO$_4$. The solvent is evaporated at 40° C. under reduced pressure and compound of formula (I) is thus obtained wherein X is chlorine. The compound is further purified by silica gel chromatography: 3 cm column diameter, 7 cm silica, elution with DCM/AcOEt=6/4.

Example 6

A single-neck flask is charged with ethyl-isonipecotate (515.6 mg; 3.28 mmoles), 9.37 ml (0.35 M) of methanol/acetic acid (9/1), LiCl (139 mg, 3.28 mmoles) are added and the 50% chloroacetaldehyde aqueous solution (386.2 mg; 4.92 mmoles) is added dropwise. The solution is cooled to 0° C. in an ice bath and NaCNBH3 (206.1 mg; 3.28 mmoles) is added portionwise. It is stirred at room temperature for 2 hrs and the development of the reaction is checked by UPLC. The solvent is evaporated at 40° C. under reduced pressure, the residue is taken up with 2N HCl (10 ml) and left under stirring for 30 min. It is extracted with AcOEt (2×20 ml), the aqueous phase is made basic with K$_2$CO$_3$, extracted with AcOEt and dried on Na$_2$SO$_4$. The solvent is evaporated at 40° C. under reduced pressure and 544.2 mg of compound of formula (I) are thus obtained wherein X is chlorine.

The invention claimed is:
1. A process for the preparation of a compound of formula (I):

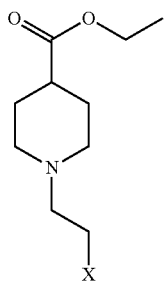

comprising carrying out a reductive amination of ethyl-isonipecotate with a X-acetaldehyde compound of the formula X—CH$_2$—CHO or acetals, hemiacetals or hydrated forms thereof, wherein X is a leaving group, in a solvent system, in the presence, or with subsequent addition, of a reducing agent.

2. The process according to claim 1, wherein X is selected from a chlorine or a bromine atom.

3. The process according to claim 1, wherein X is a chlorine atom.

4. The process according to claim 3, wherein said solvent system is selected from C$_1$—C$_4$ lower alcohols and acetonitrile.

5. The process according to claim 4, wherein said solvent is methanol or acetonitrile.

6. The process according to claim 1, wherein said solvent system also comprises a weak acid.

7. The process according to claim 6, wherein said weak acid is acetic acid.

8. The process according to claim 1, wherein said solvent system is a mixture of solvent/acetic acid =8-10/1 (v/v) or higher.

9. The process according to claim 1, wherein the process is carried out in the presence of water.

10. The process according to claim 1, wherein the ethyl-isonipecotate/X-acetaldehyde ratio is 1:1-1.5.

11. The process according to claim 1, wherein said reducing agent is selected from the group consisting of sodium cyanoborohydride (NaCNBH$_3$); sodium triacetoxy-borohydride (NaBH(OAc)$_3$); 3-pyridine-borane (pyr-BH3); Ti(Oi-Pr)$_4$/NaBH$_4$: borohydride supported on resins; Zn(BH$_4$)$_2$/SiO$_2$; Bu$_3$SnH/SiO$_2$; and phenyl-SiH$_4$/Bu$_2$SnCl$_2$.

12. The process according to claim 11, wherein said reducing agent is selected from the group consisting of sodium cyanoborohydride (NaCNBH$_3$) and sodium triacetoxyborohydride (NaBH(OAc)$_3$).

13. The process according to claim 12, wherein the molar ratios of ethyl-isonipecotate/X-acetaldehyde/sodium cyanoborohydride are 1:1-1.5:0.3-1.5.

14. The process according to claim 12, wherein the molar ratios of ethyl-isonipecotate/X-acetaldehyde/sodium triacetoxyborohydride are 1:1-1.5:4-6.

15. The process according to claim 1, wherein the reaction occurs in the presence of halogen salts.

16. The process according to claim 15, wherein the reaction occurs in the presence of an alkali metal or an alkali earth metal chloride.

* * * * *